United States Patent [19]

Jessel, Jr. et al.

[11] Plant 4,494

[45] Jan. 15, 1980

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 952,259

[22] Filed: Oct. 17, 1978

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum plant known by the cultivar name Moonwind and particularly characterized as to uniqueness by the combined characteristics of flat capitulum form; spooned daisy capitulum type; white ray floret color, devoid of pink discoloration; diameter across face of capitulum ranging from 65 to 75 mm. at maturity; uniform eight week photoperiodic flowering response to short days; medium plant height when grown as a pinched spray pot; semi-spreading branching pattern, and minimum pollen production.

1 Drawing Figure

1

The present invention comprises a new and distinct cultivar of *Chrysanthemum morifolium*, Ramat., hereinafter referred to by the cultivar name Moonwind.

Moonwind is a product of a planned breeding program which had the objective of creating new chrysanthemum cultivars with spooned daisy capitulum type, white ray floret color, seven or eight week flowering response, and with the ability to produce commerically acceptable quality in year round pot mum programs. Such traits in combination were not present in previously available commercial cultivars.

Moonwind was originated from a cross made in a controlled breeding program in Barberton, Ohio in 1975. The female parent was Frost, a white spooned daisy disclosed in our U.S. Plant Pat. No. 4,129, granted Oct. 18, 1977. The male parent was Jamboree, a bronze spooned daisy disclosed in our U.S. Plant Pat. No. 4,156, granted Nov. 22, 1977. Both Frost and Jamboree are products of the breeding program of the present inventors.

Moonwind was discovered and selected as one flowering plant within the progeny of the stated cross by Walter H. Jessel, Jr. and William E. Duffett on Nov. 19, 1976 in a controlled environment in Barberton, Ohio.

The first act of asexual reproduction of Moonwind was accomplished when vegetative cuttings were taken from the initial selection in February, 1977 in a controlled environment in Barberton, Ohio by a technician working under formulations established and supervised by Walter H. Jessel, Jr. and William E. Duffett. Continued asexual reproduction by vegetative cuttings for evaluative tests in flowering and stock programs in conjunction with horticultural examination of selected units initiated Nov. 7, 1977 has demonstrated that the combination of characteristics as herein disclosed for Moonwind are firmly fixed and are retained through successive generations of asexual reproduction.

Moonwind has not been observed under all possible environmental conditions. The phenotype may vary significantly with variations in environment such as temperature, light intensity, and daylength. The following observations, measurements, and comparisons describe plants grown in Barberton, Ohio and Salinas, Calif. under greenhouse conditions which approximate those generally used in commercial practice.

2

The following traits have been repeatedly observed and are determined to be basic characteristics of Moonwind which in combination distinguish this chrysanthemum as a new and distinct cultivar:

(1) Flat capitulum form.

(2) Spooned daisy capitulum type.

(3) White ray floret color, devoid of pink discoloration.

(4) Yellow-green (immature) to yellow (mature) disc floret color.

(5) Diameter across face of capitulum ranging from 65 to 75 mm. at maturity.

(6) Uniform eight week photoperiodic flowering response to short days.

(7) Medium plant height (requiring 1–2 long day weeks prior to pinch and short days, and two applications of 2500 ppm B-9 SP, 14 to 21 days after the beginning of short days to attain a flowered plant height of 30 to 45 cm.).

(8) Semi-spreading branching pattern.

(9) Minimum pollen production.

The accompanying photographic drawing shows typical inflorescense and foliage characteristics of Moonwind, with colors being as nearly true as possible with illustrations of this type.

Of the many commercial cultivars known to the present inventors, the most similar existing cultivar in comparison to Moonwind is the cultivar Illini Spinwheel, U.S. Plant Pat. No. 3,379. Reference is made to attached Chart A which compares certain characteristics of Moonwind to those same characteristics of Illini Spinwheel. Comparisons to the parental cultivar, Frost, are also included. General comparisons are as follows:

(1) In comparison to Illini Spinwheel, Moonwind has less tendency to discolor its ray florets with pink tinging under cool (less than 60° F.) finishing temperatures and with maturity; produces less pollen; has larger capitulum size, taller plant height, and shorter flowering response period. The ray floret color at finishing temperature of 60° F. and warmer; capitulum form; capitulum type, and branching pattern of Moonwind are similar to those of Illini Spinwheel.

(2) In comparison to Frost, Moonwind has smaller diameter across face of capitulum, greater responsiveness to B-9 SP for height control, more spreading branching pattern and shorter flowering response period. The ray floret color, capitulum form, capitulum type, pollen production, and plant height of Moonwind are similar to those of Frost.

In the following description, color references are made to A Limit Color Cadcade, by the Munsell Company, 1972 edition. The color values were determined between 10:00 and 10:30 A.M. on Aug. 11, 1978 under 100 foot-candle light intensity at Salinas, Calif.

BOTANICAL CLASSIFICATION: *Chrysanthemum morifolium,* Ramat., cv Moonwind.

I. INFLORESCENCE

A. Capitulum:
*Form.*—Flat.
*Type.*—Spooned daisy.
*Diameter across face.*—65 to 75 mm.

B. Corolla of ray florets:
*Color (abaxial).*—White.
*Color (adaxial).*—White.

C. Reproductive organs:
*Androecium.*—Present disc florets only; scant to numerous; scant pollen.
*Gynoecium.*—Present both ray and disc florets.

D. Corolla of disc florets:
*Color.*—20-10 (immature) to 26-4 (mature).

II. PLANT

A. General appearance: Semi-spreading branching pattern; medium height.

B. Foliage:
*Color (abaxial).*—Approximately 21-14 to 22-14.
*Color (adaxial).*—Approximately 21-13 overlaid with white.

CHART A

COMPARISON OF MOONWIND, ILLINI SPINWHEEL AND FROST.

| CULTIVAR | RAY FLORET COLOR | POLLEN PRO-DUCTION | BRANCHING PATTERN | CAPITULUM TYPE AND FORM | DIAMETER ACROSS FACE OF CAPITULUM | PLANT HEIGHT | FLOWERING RESPONSE PERIOD |
|---|---|---|---|---|---|---|---|
| MOONWIND | White | Sparse | Semi-spreading | Flat spooned daisy | 65 to 75 mm. | Medium, responsive to B-9 SP for height control. | 8 week |
| ILLINI SPINWHEEL | White, tinging pink with cool temperatures and age. | Abundant | Semi-spreading | Flat spooned daisy | 45 to 60 mm. | Short, responsive to B-9 SP for height control | 8 week |
| FROST | White | Sparse | Semi-spreading | Flat spooned daisy | 80 to 95 mm. | Medium, not responsive to B-9 SP for height control | 8 week |

COMPARISONS MADE OF PLANTS GROWN AS PINCHED SPRAY POTS IN BARBERTON, OHIO,AND IN SALINAS, CALIFORNIA.

We claim:

1. A new and distinct cultivar of *Chrysanthemum morifolium,* Ramat., plant known by the cultivar name Moonwind and particularly characterized as to uniqueness by the combined characteristics of flat capitulum form; spooned daisy capitulum type; white ray floret color, devoid of pink discoloration; diameter across face of capitulum ranging from 65 to 75 mm. at maturity; uniform eight week photoperiodic flowering response to short days; medium plant height when grown as a pinched spray pot; semi-spreading branching pattern; and minimum pollen production.

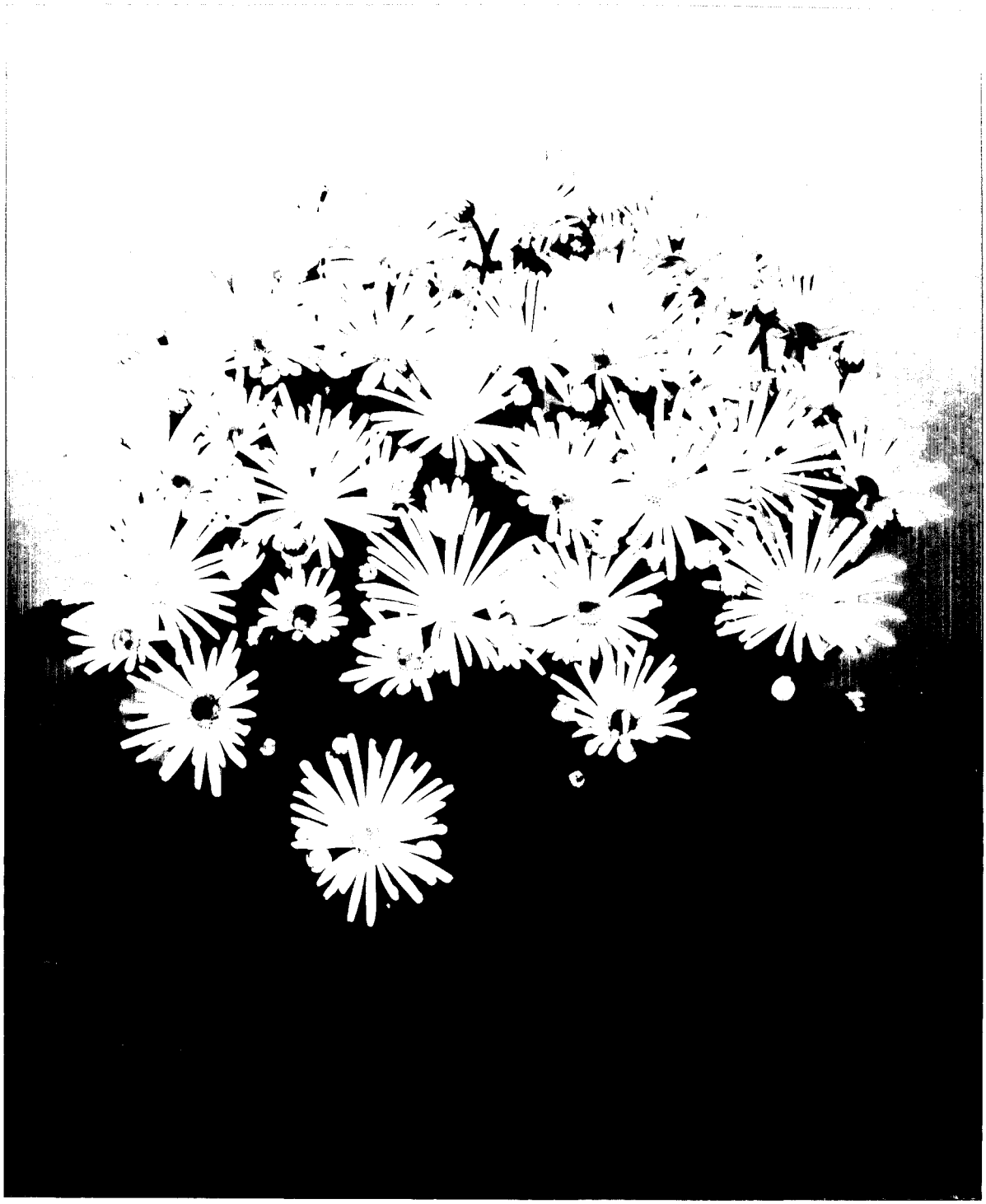

* * * * *